US011425940B2

(12) United States Patent
Kokenge

(10) Patent No.: US 11,425,940 B2
(45) Date of Patent: Aug. 30, 2022

(54) ADHESIVE SUPPORT GARMENTS

(71) Applicant: Tit Tape LLC, Cincinnati, OH (US)

(72) Inventor: Julia Kokenge, Cincinnati, OH (US)

(73) Assignee: Tit Tape LLC, Cincinnati, OH (US)

( * ) Notice: Subject to any disclaimer, the term of this patent is extended or adjusted under 35 U.S.C. 154(b) by 63 days.

(21) Appl. No.: 16/661,339

(22) Filed: Oct. 23, 2019

(65) Prior Publication Data

US 2020/0120995 A1 Apr. 23, 2020

Related U.S. Application Data

(60) Provisional application No. 62/749,385, filed on Oct. 23, 2018.

(51) Int. Cl.
*A41C 3/06* (2006.01)
*A41C 3/00* (2006.01)

(52) U.S. Cl.
CPC ............ *A41C 3/065* (2013.01); *A41C 3/0071* (2013.01)

(58) Field of Classification Search
CPC ....... A41C 3/0065; A41C 3/0071; A61F 5/03; A61F 13/14; A61F 2013/00382
USPC ...................................................... 450/56, 81
See application file for complete search history.

(56) References Cited

U.S. PATENT DOCUMENTS

| | | | | |
|---|---|---|---|---|
| 1,630,597 A | * | 5/1927 | Banff | A61F 13/0203 604/307 |
| 1,783,512 A | * | 12/1930 | Mather | A41C 3/065 450/81 |
| 2,030,135 A | * | 2/1936 | Carpenter | C09J 7/20 24/67 R |
| 2,292,024 A | * | 8/1942 | Dreher | G09F 7/18 428/317.3 |
| 2,440,426 A | * | 4/1948 | Miriam | A41C 3/0078 450/47 |
| 2,793,369 A | * | 5/1957 | Panighini | A41C 3/065 450/53 |
| 2,869,553 A | * | 1/1959 | D Or | A41C 3/065 450/81 |
| 3,280,818 A | * | 10/1966 | Pankey | A41C 3/065 450/81 |
| 3,297,036 A | * | 1/1967 | Williams | A41C 3/065 450/81 |
| 3,934,593 A | * | 1/1976 | Mellinger | A41C 3/065 450/56 |
| 4,343,313 A | * | 8/1982 | Le Jeune | A41C 3/065 450/39 |
| 4,734,320 A | * | 3/1988 | Ohira | A61F 13/0273 156/160 |
| 4,992,074 A | * | 2/1991 | Diaz | A41C 3/065 2/267 |

(Continued)

FOREIGN PATENT DOCUMENTS

| | | | | |
|---|---|---|---|---|
| DE | 10244808 A1 | * | 4/2004 | ............ A41C 3/065 |
| FR | 2738480 A1 | * | 3/1997 | ............ A41C 3/065 |

*Primary Examiner* — Jocelyn Bravo
(74) *Attorney, Agent, or Firm* — Dinsmore & Shohl LLP

(57) ABSTRACT

In one embodiment, an adhesive support garment includes a base anchoring portion and a shaping panel. The base anchoring portion is configured to be adhered to a body beneath a breast. The shaping panel includes a fabric layer and an adhesive layer that is configured to extend from the base anchoring portion over the breast and adhere thereto. The shaping panel is configured to hold and orient the breast.

11 Claims, 11 Drawing Sheets

(56) References Cited

U.S. PATENT DOCUMENTS

| | | | | |
|---|---|---|---|---|
| 5,755,611 | A * | 5/1998 | Noble | A41C 3/065 450/39 |
| 5,938,631 | A * | 8/1999 | Colman | A61F 13/108 602/75 |
| 5,998,693 | A * | 12/1999 | Zagame | A61F 13/145 602/52 |
| 6,257,951 | B1 * | 7/2001 | DeMarco | A41C 3/0078 450/41 |
| 6,397,391 | B2 * | 6/2002 | DeMarco | A41C 3/0078 2/8.1 |
| 6,857,935 | B1 * | 2/2005 | Dohan | A41C 3/065 2/244 |
| 7,229,335 | B2 * | 6/2007 | Davis | A41C 3/065 450/54 |
| 7,404,752 | B1 * | 7/2008 | Karon | A41C 3/12 2/53 |
| 7,637,798 | B2 * | 12/2009 | Lutzi | A41C 3/065 450/37 |
| 7,993,182 | B2 * | 8/2011 | Horton | A41C 3/065 450/81 |
| 8,042,194 | B2 * | 10/2011 | Connor | A61F 13/47236 2/46 |
| 9,706,797 | B1 * | 7/2017 | Kratsa | A41C 3/065 |
| 10,058,132 | B2 * | 8/2018 | Harris | A41C 3/065 |
| 10,111,473 | B2 * | 10/2018 | Kratsa | A41C 3/0028 |
| 2001/0021620 | A1 * | 9/2001 | DeMarco | A41C 3/0078 450/81 |
| 2001/0049250 | A1 * | 12/2001 | Johnson | A41C 3/065 450/81 |
| 2002/0040202 | A1 * | 4/2002 | Levin | A61F 13/0203 602/43 |
| 2002/0187727 | A1 * | 12/2002 | Pinna | A41C 3/065 450/81 |
| 2003/0129343 | A1 * | 7/2003 | Galkiewicz | C09J 7/38 428/40.1 |
| 2003/0185706 | A1 * | 10/2003 | Ribi | G01N 31/229 422/401 |
| 2004/0057747 | A1 * | 3/2004 | Michlin | G03G 15/0884 399/106 |
| 2004/0134596 | A1 * | 7/2004 | Rosati | B05C 1/0813 156/230 |
| 2004/0192164 | A1 * | 9/2004 | Ajili | A41C 3/065 450/38 |
| 2005/0059320 | A1 * | 3/2005 | Valentin | A41C 3/065 450/81 |
| 2005/0186885 | A1 * | 8/2005 | Valentin | A41C 3/065 450/81 |
| 2005/0221719 | A1 * | 10/2005 | Chou | A41C 3/065 450/81 |
| 2005/0282468 | A1 * | 12/2005 | Davis | A41C 3/065 450/81 |
| 2006/0089085 | A1 * | 4/2006 | Ruggiero | A41D 7/00 450/81 |
| 2006/0252342 | A1 * | 11/2006 | Davis | A41C 3/065 450/41 |
| 2006/0288463 | A1 * | 12/2006 | Bernard | A41D 27/12 2/46 |
| 2007/0218805 | A1 * | 9/2007 | Mateo | A41C 3/065 450/81 |
| 2008/0066209 | A1 * | 3/2008 | Kayerod | G02C 5/008 2/15 |
| 2009/0117825 | A1 * | 5/2009 | Lutzi | A41C 3/065 450/81 |
| 2009/0182256 | A1 * | 7/2009 | Lin | A61F 13/0273 602/54 |
| 2010/0294286 | A1 * | 11/2010 | Bellamy | A61M 25/02 128/887 |
| 2010/0298747 | A1 * | 11/2010 | Quinn | A61F 13/023 602/1 |
| 2012/0266348 | A1 * | 10/2012 | Meginnis | A41D 31/0005 2/69 |
| 2014/0273739 | A1 * | 9/2014 | Chang | A41C 3/065 450/81 |
| 2016/0157529 | A1 * | 6/2016 | Hoeven | A41B 11/128 2/240 |
| 2018/0027886 | A1 * | 2/2018 | Kratsa | A41C 3/065 |
| 2018/0360134 | A1 * | 12/2018 | Wang | A41C 3/065 |
| 2019/0200681 | A1 * | 7/2019 | Karon | A41C 3/065 |
| 2021/0145083 | A1 * | 5/2021 | Morrow Contreras | A41C 3/144 |

* cited by examiner

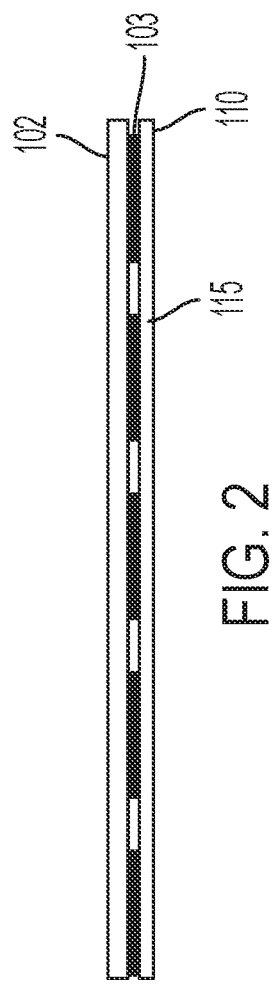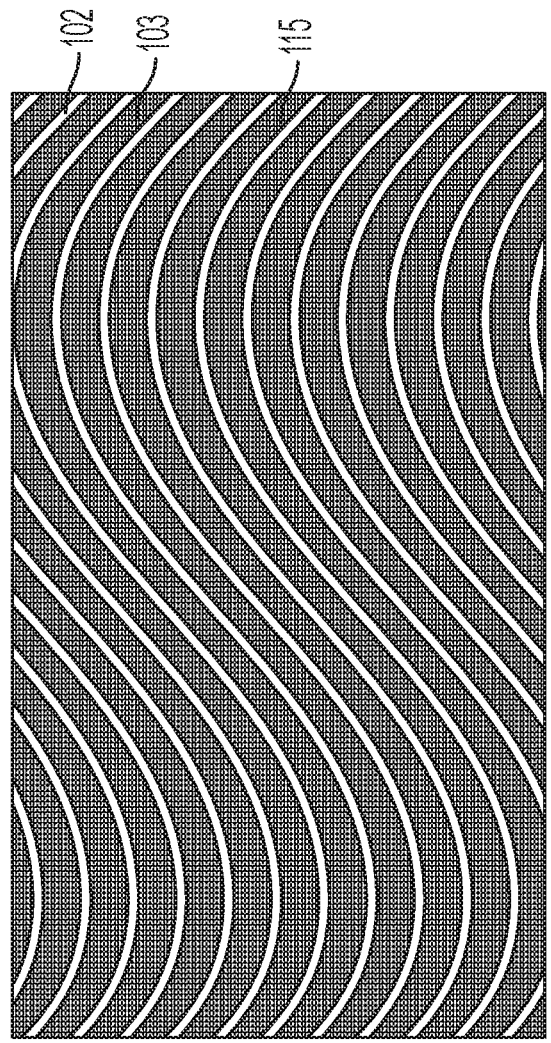

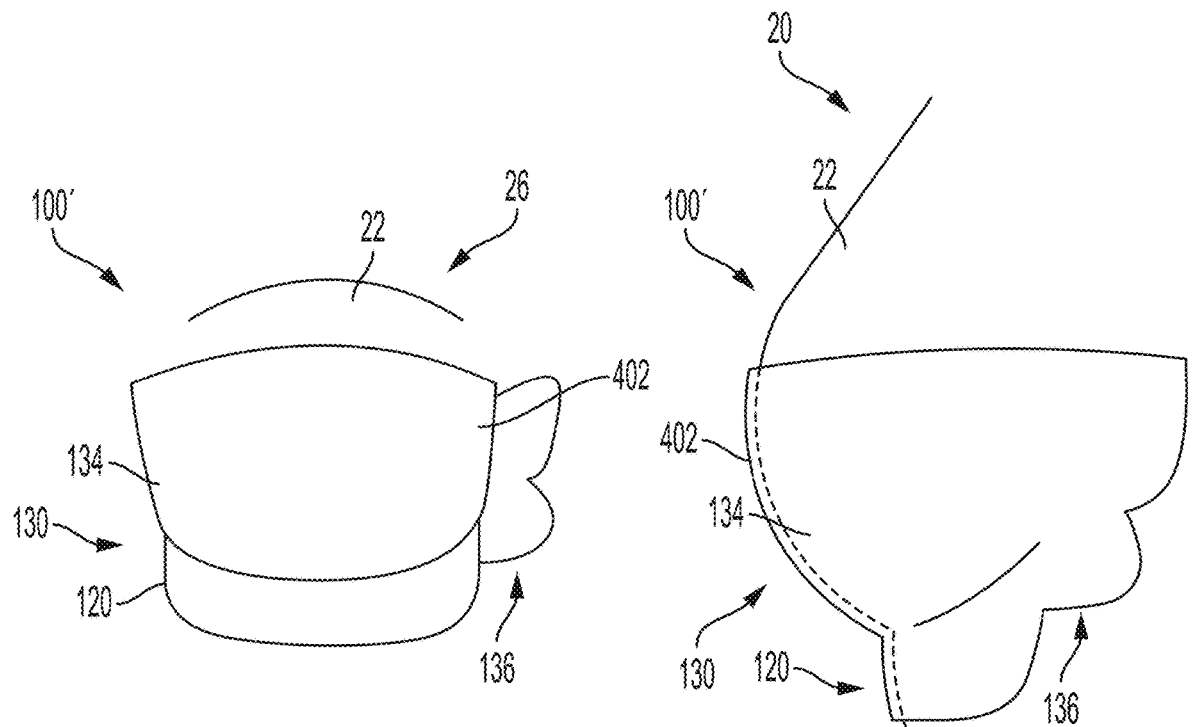
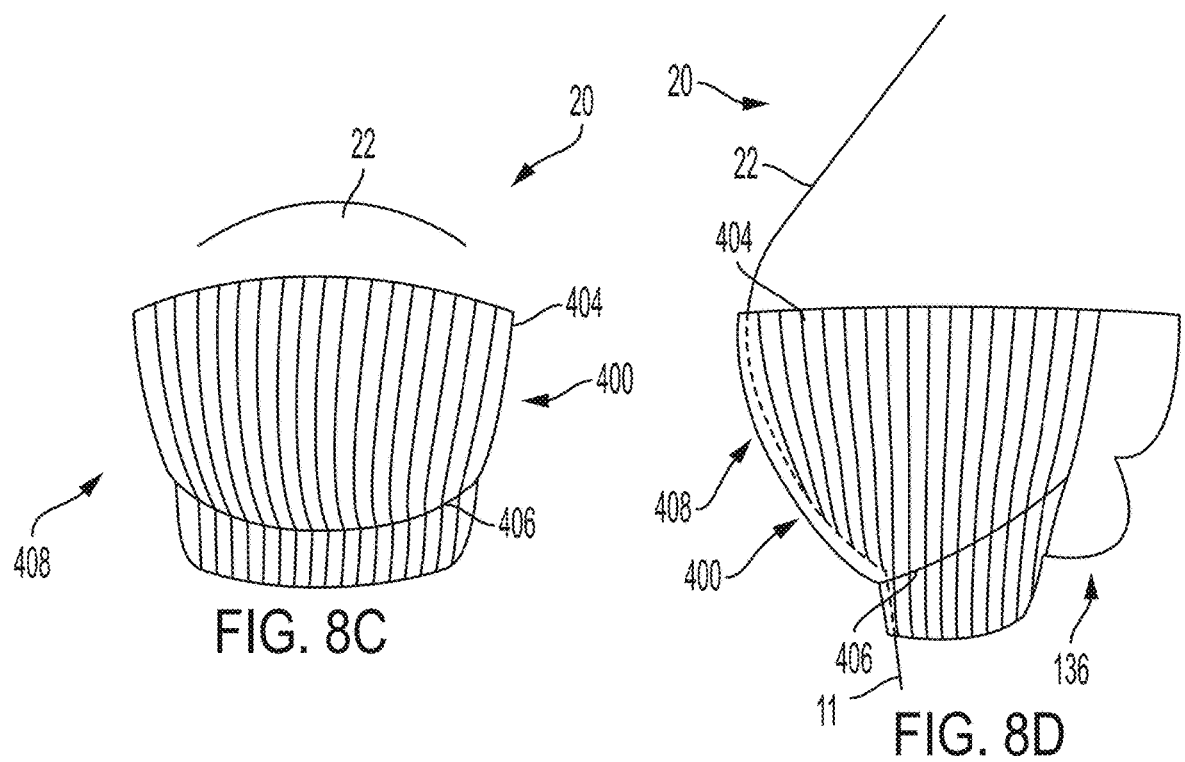

ADHESIVE SUPPORT GARMENTS

CROSS-REFERENCE TO RELATED APPLICATIONS

The present specification claims the benefit of U.S. Provisional Patent Application Ser. No. 62/749,385, entitled "Adhesive Support Garments," filed Oct. 23, 2018, hereby incorporated by reference in its entirety.

TECHNICAL FIELD

The present specification generally relates to adhesive support garments and, more specifically, adhesive support garments that comfortably provide coverage, lift, and support to breast tissue.

BACKGROUND

Over the years fashion has trended to more revealing clothing with, for example, plunging necklines and/or backless garments. When wearing such garments, it is generally preferred that any support garments (e.g., bras) not be visible. Accordingly, traditional bras that completely encircle the wearer's trunk are undesirable in such circumstances. On the market are adhesive cups that adhere to a person's breasts. However such cups are limited in that they do not provide lift or support. Additionally, these cups may lose adhesive strength during wear leading to failure (e.g., peeling off or loss of support) and/or possible wardrobe malfunctions. Furthermore, such cups often have front closures that make wearing such cups with plunging necklines undesirable. In some cases, various fashion icons (and non-public figures a-like) have resorted to using complex layers of gaffer's tape which is capable of adhering to the skin to mold their breasts to the desired shape for a particular garment. Such application of tape may be uncomfortable, time consuming, complex, and tedious.

Accordingly, a need exists for alternative adhesive support garments that comfortably provide coverage, lift, and support to breast tissue. Additionally, a need exists for adhesive support garments that last for the duration of wear, without loss of support.

SUMMARY

In one embodiment, an adhesive support garment includes a base anchoring portion and a shaping panel. The base anchoring portion is configured to be adhered to a body beneath a breast. The shaping panel includes a fabric layer and an adhesive layer and is configured to extend from the base anchoring portion over the breast and adhere thereto. The shaping panel is configured to hold and orient the breast.

In yet another embodiment, an adhesive support garment includes a first base anchoring portion, a first shaping panel, a second base anchoring portion, and a second shaping panel. The first base anchoring portion is configured to be adhered to a body beneath a first breast. The first shaping panel is configured to extend from the first base anchoring portion over the first breast and adhere thereto, wherein the first shaping panel is configured to hold and orient the first breast. The second base anchoring portion is configured to be adhered to the body beneath a second breast. The second shaping panel is configured to extend from the second base anchoring portion over the second breast and adhere thereto, wherein the second shaping panel is configured to hold and orient the second breast. Each of the first shaping panel and the second shaping panel includes a fabric layer and an adhesive layer.

In yet another embodiment, a method of applying an adhesive support garment includes attaching a base anchoring portion to a torso of a user beneath a breast of the user, and attaching a shaping panel to the breast, the shaping panel including a fabric layer and an adhesive layer extending from the base anchoring portion, wherein the shaping panel holds and orients the breast.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 2 depicts a cross-section of an adhesive support garment, according to one or more embodiments shown and described herein;

FIG. 3 depicts a woven fabric layer and an adhesive layer of an adhesive support garment, according to one or more embodiments shown and described herein;

FIG. 8A depicts a strapless adhesive support garment, according to one or more embodiments shown and described herein;

FIG. 8B depicts a side view of the strapless adhesive support garment of FIG. 6A, according to one or more embodiments shown and described herein;

FIG. 8C depicts internal structure of the strapless adhesive support garment of FIG. 8A, according to one or more embodiments shown and described herein; and FIG. 8D depicts a side view of the adhesive support garment of FIG. 8C, according to one or more embodiments shown and described herein.

DETAILED DESCRIPTION

The embodiments described herein are directed to adhesive support garments, methods of application, and methods of manufacture. In particular, the adhesive support garments described herein allows a user to wear attire that would otherwise reveal traditional support garments (e.g., bras having straps and a horizontal band) while having desired coverage, lift, and support. Such adhesive support garments are also substantially seamless under clothing so as to provide a wearer with a desired, smooth silhouette. For example, in various embodiments, an adhesive support garment may include a base anchoring portion and a shaping panel. The base anchoring portion may be configured to be adhered to a body of a user beneath the user's breast. The shaping panel may extend from the base anchoring portion over the breast and adhere thereto to hold, support, and orient the user's breast tissue in a desired configuration. As will be described in greater detail herein, such adhesive support garments may be worn beneath attire having plunging necklines and/or backless ensembles while remaining unseen. Furthermore, such adhesive support garments may be easy to apply such that a user may apply the garment to oneself without the need for additional help from others. These and additional features will be described in greater detail below.

Figure 1:
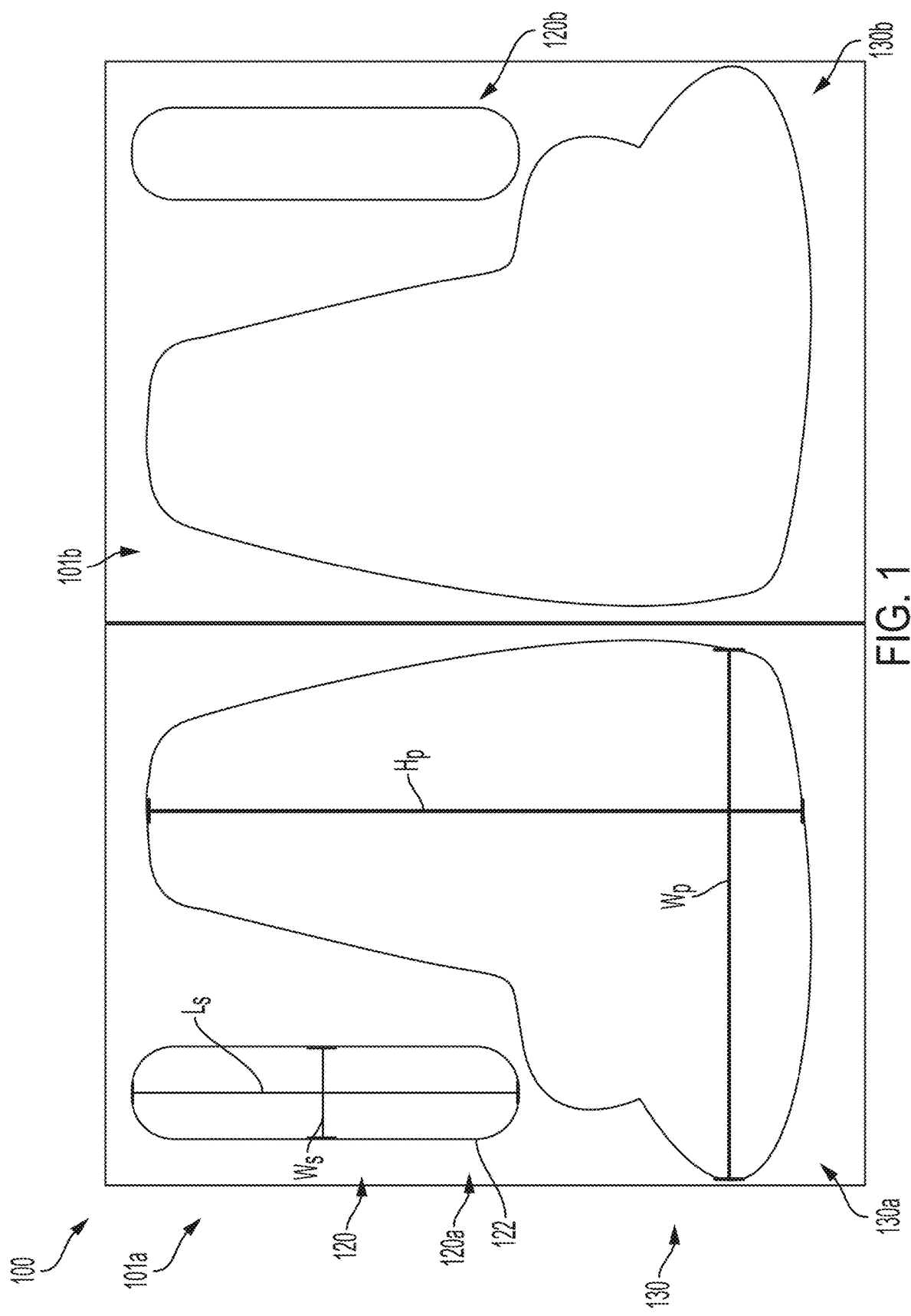
FIG. 1 depicts an adhesive support garment, according to one or more embodiments shown and described herein.

Referring now to FIG. 1, an embodiment of the adhesive support garment 100 is generally depicted. The adhesive support garment 100 may be used to support an individual's breast tissue at a desired position (e.g., with the preferred amount of coverage, support, cleavage, and lift). Accordingly, the adhesive support garment 100 may replace traditional bras or the like.

The adhesive support garment 100 may be made from an adhesive fabric (e.g., a medical grade adhesive fabric). For example the adhesive support garment 100 may be made from kinesiology tape (e.g., Kinesio® tape) or other adhesive fabrics produced in wide enough swaths from which to cut (e.g., with a CNC machine) the adhesive support garment 100. Referring to FIG. 2, an exaggerated cross-section of a portion of the adhesive support garment 100 is depicted. The adhesive support garment 100 may include a woven fabric layer 102, an adhesive layer 103 bonded to the fabric layer 102, and a backing layer 110, which may be removed to expose the adhesive layer 103 for application.

The woven fabric layer 102 may include a breathable fabric such as for example cotton, polyester, nylon, rayon, linen, silk, etc. In embodiments, the woven fabric layer 102 may include elastic fibers interwoven in the woven fabric layer 102 to allow for the woven fabric layer 102 to stretch. As will be described in greater detail herein, various portions of the woven fabric layer 102 may be woven to be elastic in one or more directions and relatively inelastic along other directions in comparison. As used herein, a material that is "elastic" is stretchable and can return to its original length or size. The woven fabric layer 102 may be made in a variety of colors and/or shades (e.g., beige, brown, black, etc.). The color and/or shade of the woven fabric layer 102 may be based on the pigment of the wearer's skin. Accordingly, the adhesive support garment 100 may blend in with the wearer's skin tone so as to be substantial inconspicuous under sheer or see-through clothing.

The adhesive layer 103 may include a medical grade adhesive such as a heat activated acrylic adhesive. However, other adhesives are contemplated including, but not limited to acrylics, silicone, polyurethane, and bio adhesives. The adhesive layer 103 be pressure sensitive. The adhesive layer 103 may be patterned on the fabric such that there is spacing between distinct adhesive locations. For example as illustrated in FIG. 3, adhesive layer 103 applied to a woven fabric layer 102 is patterned in a wave pattern. Such patterning may aid in positioning the breast tissue while also providing breathability. For example, the patterning of the adhesive layer 103 may be such so as not to restrict stretching of the woven fabric layer 102. While in some embodiments, the adhesive layer 103 may be patterned over the entire woven fabric layer 102, in some embodiments, portions of the woven fabric layer 102 may not have adhesive applied thereto. For example, in some embodiments, only a perimeter of the different components of the adhesive support garment 100 may have adhesive applied thereto. In some embodiments, the adhesive layer 103 may allow for removal and reapplication of the adhesive support garment 100 without unduly impacting the effectiveness of the adhesive layer 103. The adhesive layer 103 may define a tissue attachment surface 115 for the base anchoring portion 120 and or the shaping panel 130. In some embodiments, positioning of the adhesive layer 103 may be selected to affect elastic characteristics of the base anchoring portion 120 and/or the shaping panel 130. For example, strips of adhesive may be applied to restrict elasticity along a length direction of the elastic strip. It is noted that though the description refers throughout to an adhesive layer, such adhesive layers may not be limited to the use of adhesives. For example, the adhesive layer may include other mechanical fasteners (e.g., hook and loop materials, combinations of mechanical and adhesive fasteners, etc.) for assembling the adhesive support garment 100 to a user's body.

As will be described in greater detail herein, the backing layer 110 may include a paper backing layer, which may be easily removed to expose the adhesive layer 103 for application to a body. In some embodiments, and as will be described in greater detail herein, the backing layer 110 may be removed in distinct sections and provide instruction as to application of the adhesive support garment 100. Such integrated instruction, may ensure proper application without corrupting the adhesive due to repeated application and/or removal of the adhesive support garment 100 and/or pre-stretching components or sections of the adhesive support garment 100.

Referring again to FIG. 1, the adhesive support garment 100 may include a base anchoring portion 120 configured to be adhered to a body beneath a breast, and a shaping panel 130 configured to extend from the base anchoring portion 120 over the breast and adhered thereto. When in position, the shaping panel 130 is configured to hold and orient the breast in a position as desired by the user. The base anchoring portion 120 and the shaping panel 130 are illustrated as separate components. However, it is contemplated that the base anchoring portion 120 and the shaping panel 130 may be formed integrally with one another. That is, the base anchoring portion 120 may be interwoven with the shaping panel 130.

To accommodate two-breasted users, the adhesive support garment 100 may include a first breast support portion 101a having a first base anchoring portion 120a and a first shaping panel 130a and a second breast support portion 101b having a second base anchoring portion 120b and a second shaping panel 130b. The first breast support portion 101a may be separate from the second breast support portion 101b such that each breast may be individually positioned and supported by the adhesive support garment 100. The first shaping panel 130a and the second shaping panel 130b may generally mirror one another so as to be applied to opposite breasts. However, is it contemplated that the first shaping panel 130a and the second shaping panel 130b may be sized and/or shaped for support of different sized breasts, as the wearer may not have symmetrically sized breasts. In the remaining description when describing aspects of the shaping panel 130, the description is applicable to the first and second shaping panels 130a, 130b unless otherwise noted or apparent from the figures.

Figure 4B:
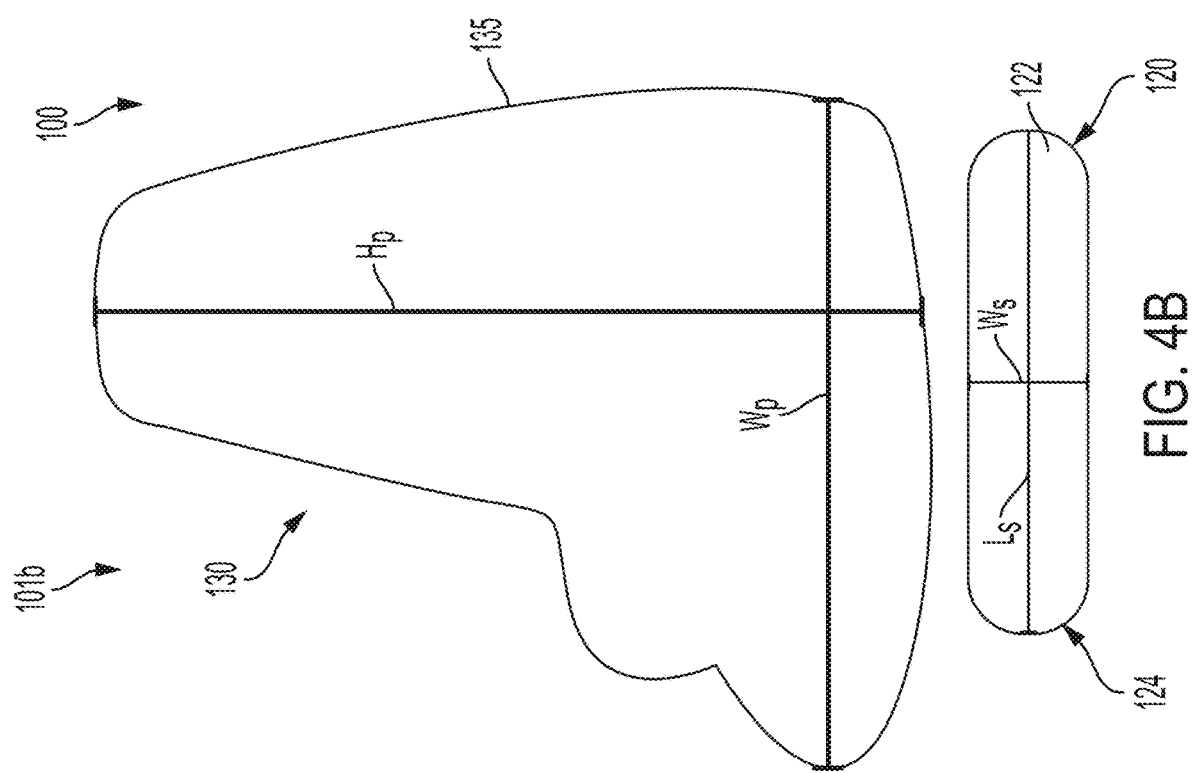
FIG. 4B depicts a front side view of the adhesive support garment of FIG. 1, according to one or more embodiments shown and described herein.
Figure 4A:
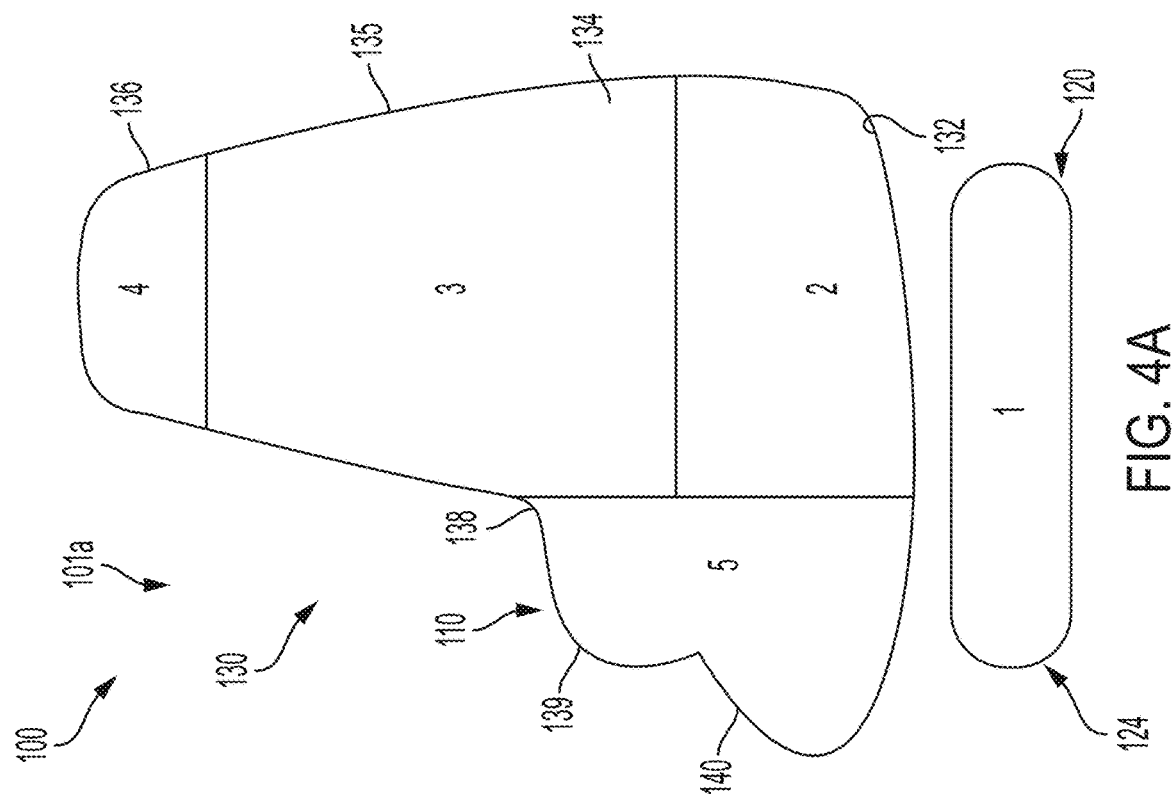
FIG. 4A depicts a backside of the adhesive support garment of FIG. 1, according to one or more embodiments shown and described herein.

FIGS. 4A and 4B illustrate a back of the first breast support portion 101a and a front view of the second breast support portion 101b, respectively. As noted above, the back of the second breast support portion 101b may be substantially identical (though mirror imaged) of the back of the first breast support portion 101a. However, each of the first breast support portion 101a and the second breast support portion 101b may differ in size and/or shape depending on the wearer's particular measurements for each breast. Each breast support portion includes a base anchoring portion 120 and a shaping panel 130.

As noted above, the base anchoring portion 120 is configured to be adhered to the body of the user beneath the breast. For application, the base anchoring portion 120 may include the tissue attachment surface 115 (beneath the backing layer 110), and opposite the tissue attachment surface 115, a panel attachment surface 122. The panel attachment surface 122 may allow the shaping panel 130 to securely adhere thereto, such as illustrated in FIGS. 5C and 5D.

In embodiments, wherein the base anchoring portion 120 is separate from the shaping panel 130, the base anchoring portion 120 may, as illustrated in the figures, be an elongate strip 124. The elongate strip 124 may have a strip width, $W_s$, and a strip length, $L_s$, that is greater than the strip width, $W_s$. Stated another way, the elongate strip 124 may longer in a strip length direction as indicated by $L_s$, than the strip is wide in the strip width direction as indicated by $W_s$. The elongate strip 124 may be configured (e.g., woven) such that the elongate strip 124 is elastically deformable (e.g., stretchable) along the strip length direction and relatively inelastic along the strip width direction compared to the strip length direction. Accordingly, during application a leading portion of the elongate strip 124 may be placed at the desired position. Thereafter, the remaining portion of the elongate strip 124 may be stretched before adherence to the user's skin, wherein upon application the elongate strip 124 applies a gentle pulling force to the skin by virtue of the elongate strip's 124 elastic force (e.g., the elongate strip's 124 tendency to return to its original shape). The elasticity of the elongate strip 124 may also allow the user freedom of motion to bend, stretch, twist, and the like without causing discomfort or inadvertent separate of the elongate strip 124 from the body. The elasticity may also allow for natural movement of breast tissue vertically while securing a preventing or restricting lateral movement. The various edges of the base anchoring portion 120 may be rounded to provide comfort and smooth application for the user.

As noted above, the elongate strip 124 may be relatively inelastic in the strip width direction. Accordingly, upon application the elongate strip 124 may provide a secure base upon which to attach the shaping panel 130.

Figure 5A:
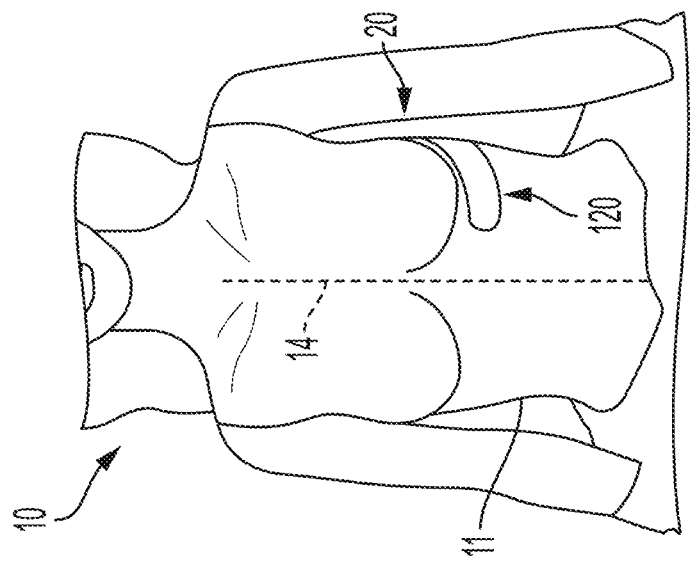
FIG. 5A depicts a user prior to application of the adhesive support garment, according to one or more embodiments shown and described herein.
Figure 5B:
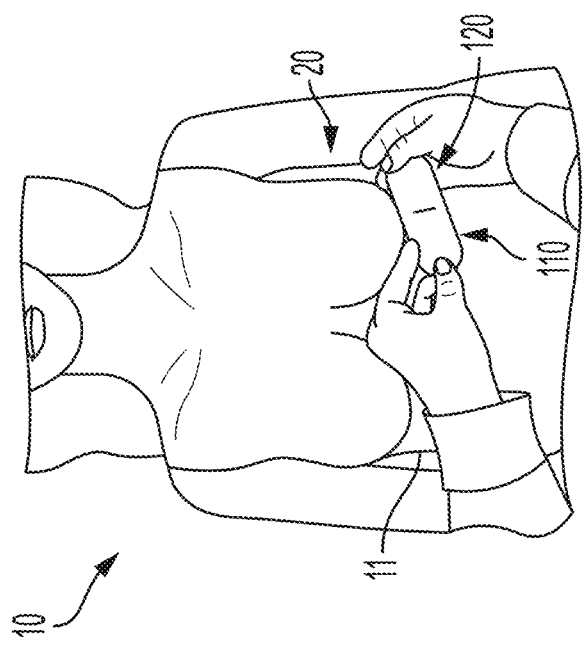
FIG. 5B depicts application of a base anchoring portion of the adhesive support garment, according to one or more embodiments shown and described herein.
Figure 5D:
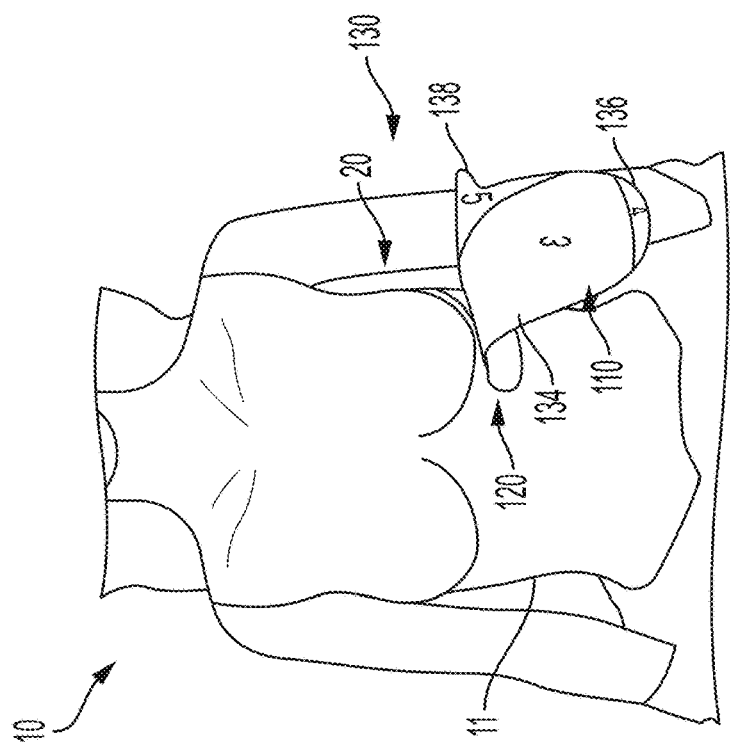
FIG. 5D depicts application of the panel anchor portion of the shaping panel of the adhesive support garment, according to one or more embodiments shown and described herein.
Figure 5C:
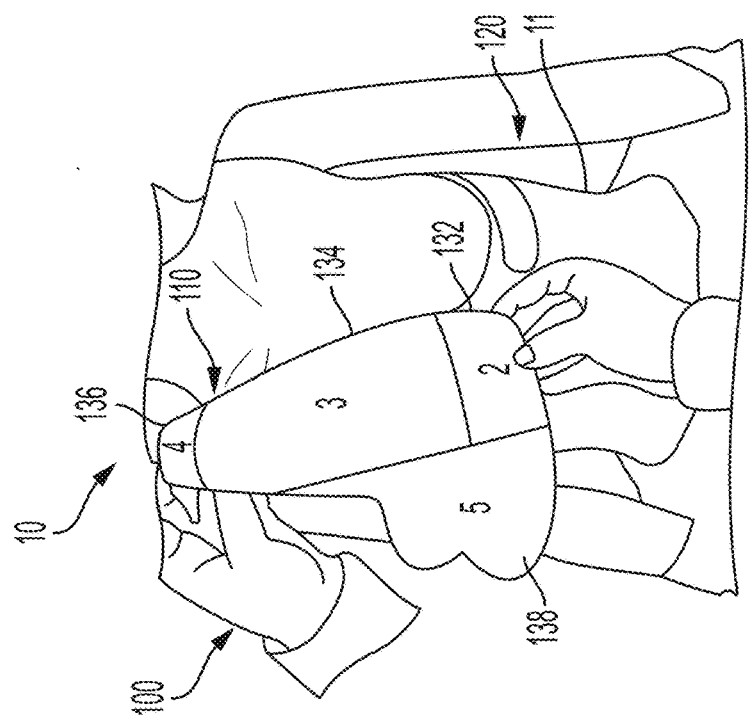
FIG. 5C depicts pre-application of a panel anchor portion of a shaping panel of the adhesive support garment, according to one or more embodiments shown and described herein.

Such attachment is illustrated in FIGS. 5A and 5B depict application of the base anchoring portion 120 to a user 10. As illustrated the base anchoring portion 120 is secured to the user 10 directly beneath the user's breast 20. The base anchoring portion 120 may be positioned as close to the user's midline 14 (e.g., the centerline of the body) as the user wishes depending on the amount of coverage the user desires. For example, for fashions with plunging necklines, the user may position the base anchoring portion 120 at a position such that the base anchoring portion 120 is hidden beneath the user's attire.

Still referring to FIGS. 4A and 4B, the shaping panel 130 is configured to be adhered to the user's breast and secured so as to lift and shape the user's breast as desired. The shaping panel 130 includes a panel width, $W_p$, and a panel height, $H_p$, the panel height may be greater than the panel width. However, as will be discussed in greater detail, the size of various portions of the shaping panel 130 may be adjusted based on cup size (traditional bra cup size A, B, C, D, etc., as well as any size in between) and band size (e.g., 32, 24, 26, etc., as well as any size in between). As used herein, the terms "height" and "width" refer to height and width directions as positioned on a wearer. The shaping panel 130 may be elastically deformable along the panel height direction and relatively inelastic along the panel width direction. Elasticity in the vertical direction may provide a user the ability to adjust the degree of lift and positioning of the breast comfortably while not unduly restrict the user's shoulder motion. Furthermore, this allows for natural movement of the breast tissue vertically while securing and preventing lateral movement. That is, by restricting horizontal stretching the breast may be better secured in place relative to the clothing worn by the user. For example, preventing horizontal stretching allows the user to ensure the breast 20 stays in position throughout wear.

FIG. 4A illustrates the backing layer 110 positioned over the shaping panel 130 and the base anchoring portion 120. For illustrative purposes various portions of the backing layers are labeled 1-5 to indicate various portions of the adhesive support garment 100. Other labeling schemes are also contemplated and possible (e.g., A-E, I-V, etc.). It is noted that the labeling may indicate the order of application of the various components of the adhesive support garment 100. For example, label 1 indicates the base anchoring portion 120 and such label may illustrate that the base anchoring portion 120 may be applied first.

Referring specifically to the shaping panel 130 there are illustrated four discrete sections each having a labeled backing section. Though four sections are illustrated, a fewer or greater number of sections are contemplated and possible. For example, the shaping panel 130 may include a panel anchor portion 132, indicated by labeled backing section 2, a lifting panel portion 134, indicated by labeled backing section 3, a vertical grip and support tab 136, indicated by labeled backing section 4, and a lateral support tab 138, indicated by labeled backing section 5.

The panel anchor portion 132 may be configured to adhere to the base anchoring portion 120 as illustrated in FIGS. 5C and 5D. As will be described in greater detail below, as the adhesive support garment 100 is applied, portions of the backing layer 110 corresponding to the labeled sections are removed. As illustrated, the panel anchor portion 132 is adhered to the base anchoring portion 120 to provide a base from which to stretch and position the shaping panel 130. Further, the adhesive layer 103 of the material of the shaping panel 130 may form a stronger bond with the base anchoring portion 120 than if the shaping panel 130 were directly contacted to skin due, at least in part, to the material forming the base anchoring portion 120. However, as noted above, embodiments may include an integral base anchoring portion as part of the shaping panel 130. The length and height of the panel anchor portion 132 may be based on the cup size of the user. For example, a larger base anchoring portion 120 having more contact area may provide a stronger anchor for larger breasted users, whereas a smaller breasted user may not need as larger an anchor. That is, the base anchoring portion 120 may be sized and shaped to be anchored to the skin surface over substantially its entire area at a location beneath the breast.

Figure 5F:
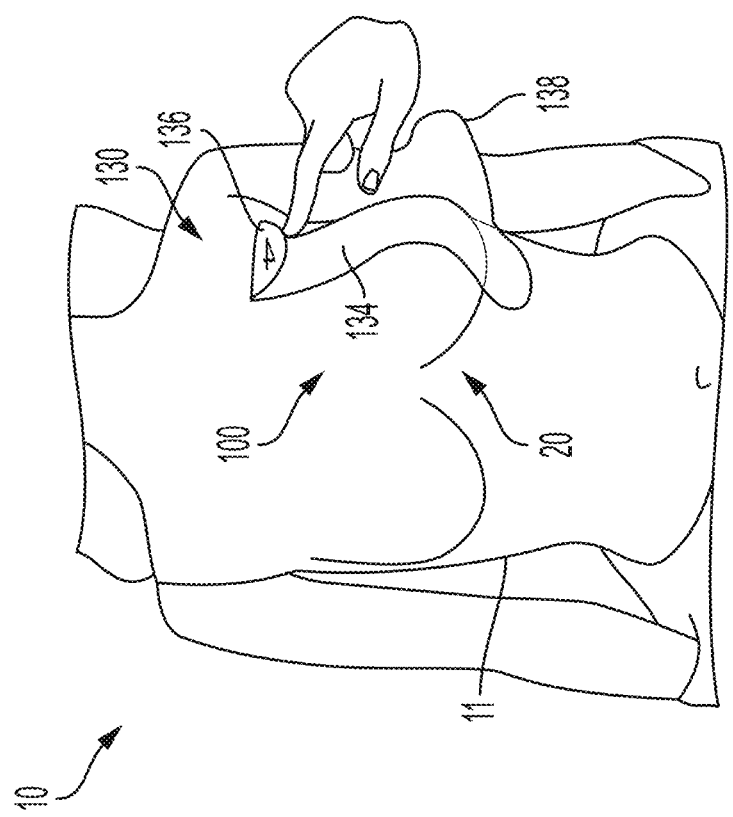
FIG. 5F depicts application of the lifting panel portion of the shaping panel, according to one or more embodiments shown and described herein.
Figure 5E:
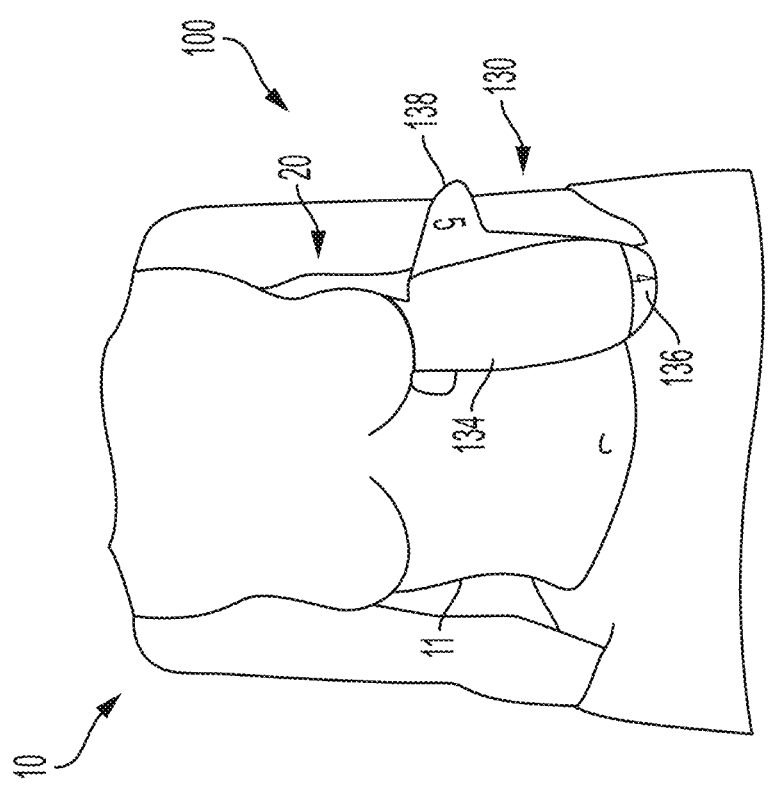
FIG. 5E depicts pre-application of a lifting panel portion of the shaping panel, according to one or more embodiments shown and described herein.
Figure 5H:
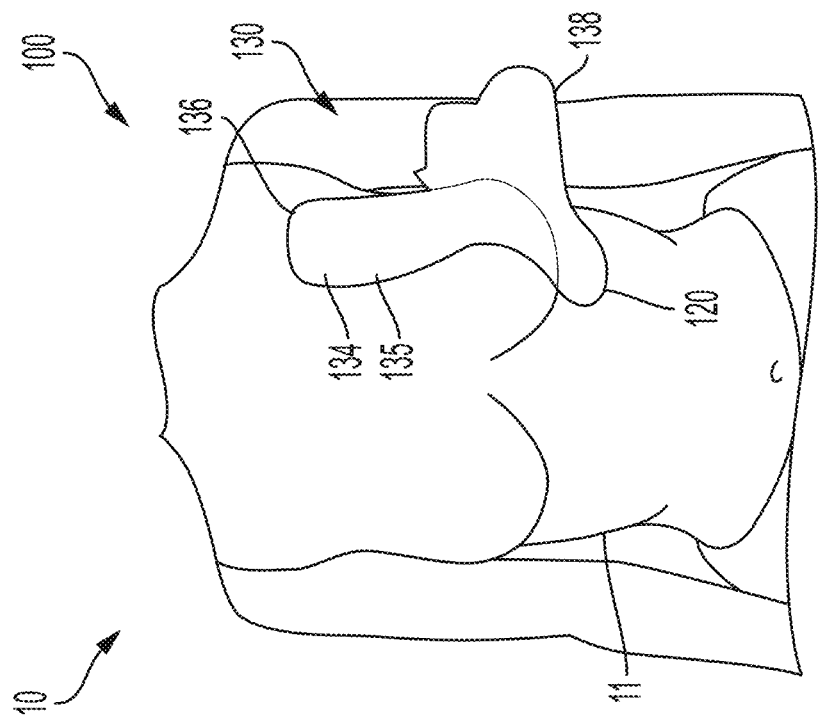
FIG. 5H depicts application of the vertical grip and support tab of the shaping panel, according to one or more embodiments show and described herein.
Figure 5G:
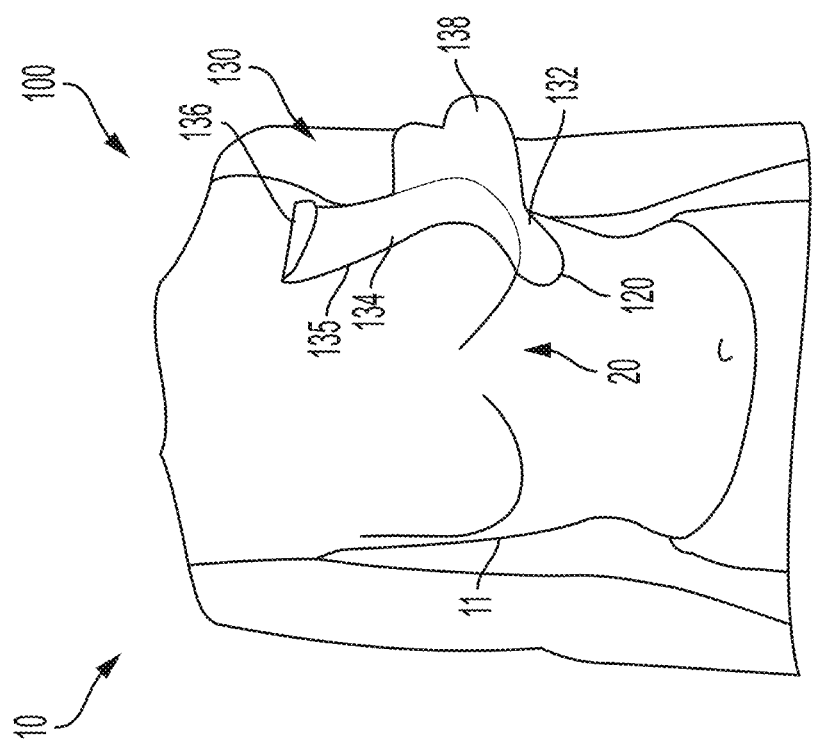
FIG. 5G depicts pre-application of a vertical grip and support tab of the shaping panel, according to one or more embodiments shown and described herein.

The lifting panel portion 134 may extend from the panel anchor portion 132 along the height direction of the shaping panel 130. The lifting panel portion 134 may be stretched and smoothed over the breast 20 to lift the breast 20 to a desired location, as illustrated in FIGS. 5E and 5F. The overall size (e.g., the height and the width) of the lifting panel portion 134 may be dependent on the cup size of the user. For example, a larger breasted user may need additional coverage as well as holding force that may be provided by a larger surface area. A side edge 135 of the lifting panel portion 134 (e.g., the edge directed along the midline of the body when applied, may be curved and tapered toward the top of the lifting panel portion 134. Such tapering and curvature may provide a smooth transition between exposed skin and covered breast tissue so that tissue does not protrude beyond the lifting panel portion 134 to provide a lumpy appearance. Instead the silhouette may remain smooth. In some embodiments, a height of the lifting panel portion 134 may be reduced to accommodate a strapless garment, such as illustrated in FIGS. 6A-8D. That is, the lifting panel portion 134 may extend over a portion of the breast 20 such that an upper portion 22 of the breast 20 is exposed (e.g., a portion of breast tissue located above the user's nipple). Such embodiments may also lack a vertical grip and support tab 136, described below.

Extending from the lifting panel portion 134 may be the vertical grip and support tab 136. The vertical grip and support tab 136 may provide additional fortification and holding force to secure the breast 20 in the lifted position. Additionally, the vertical grip and support tab 136 may provide a portion of the shaping panel 130 in conjunction with the removable backing layer 110 which may be gripped for application while avoid touching adhesive layer 103 or pre-stretching the vertical grip and support tab 136 prior to application to the wearer's breast. Application of the vertical grip and support tab 136 is illustrated in FIGS. 5E and 5F. The vertical grip and support tab 136 may have a width equal to that of the lifting panel portion 134 such that the transition between the lifting panel portion 134 and the vertical grip and support tab 136 is smooth and seamless (e.g., without sharp corners). The vertical grip and support tab 136 may have a round top edge to provide additional comfort and to prevent unintended catching on other articles as sharp edges tend to.

Figure 5J:
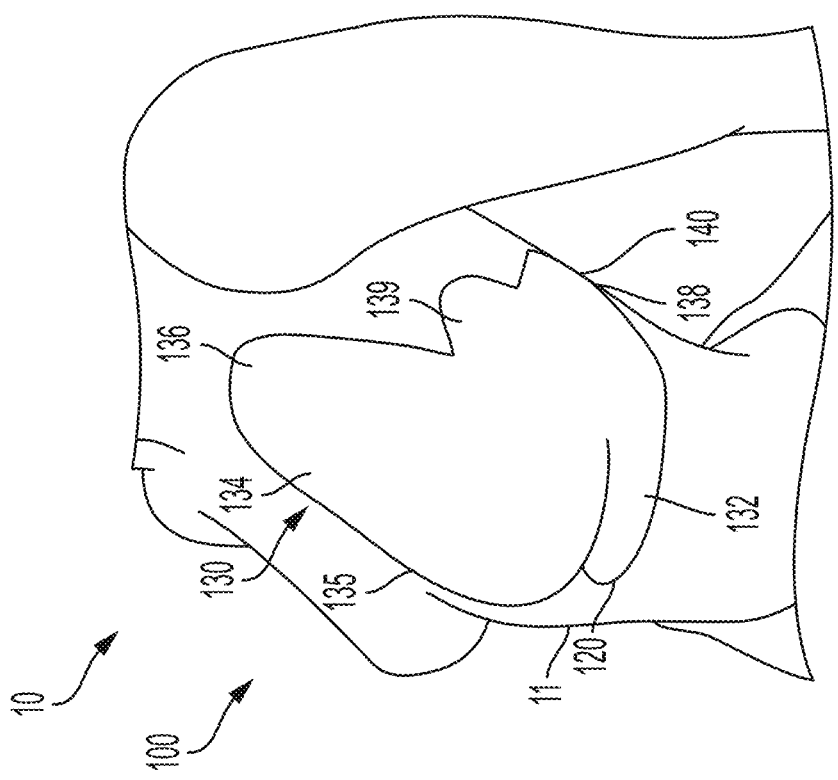
FIG. 5J depicts application of the lateral support tab of the shaping panel, according to one or more embodiments shown and described herein.
Figure 5I:
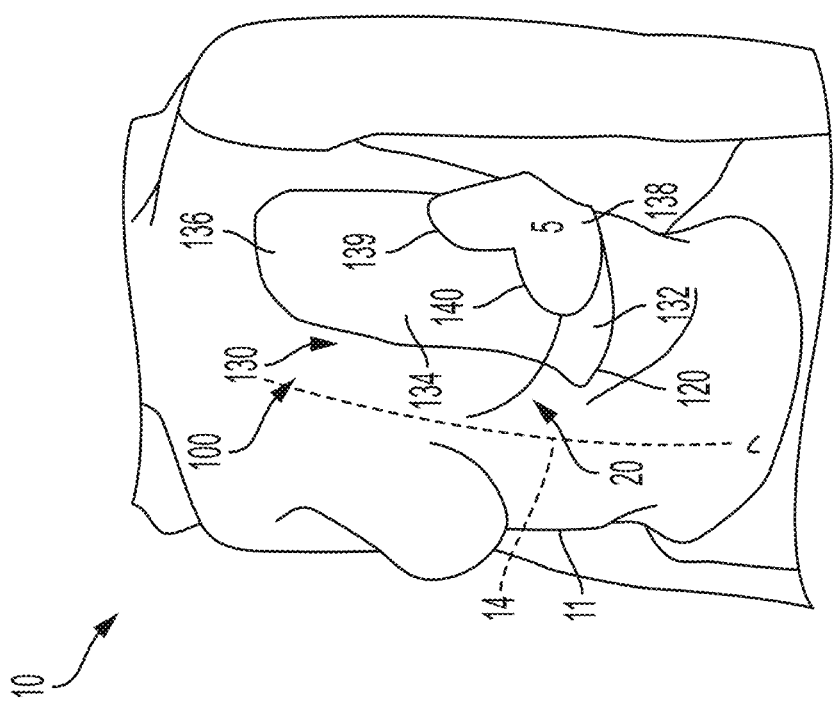
FIG. 5I depicts pre-application of a lateral support tab of the shaping panel, according to one or more embodiments shown and described herein.

Referring again to FIGS. 4A-4B, extending laterally (e.g., in the panel width direction) from the lifting panel portion 134 may be the lateral support tab 138. The lateral support tab 138 may allow the user to secure the breast 20 in position so as to provide the desired amount of cleavage. For example, the breast 20 may be pushed toward the midline 14 of the body before securing the lateral support tab 138 to reflect the desired amount of cleavage. Accordingly, because the shaping panel 130 may be relatively inelastic in the widthwise direction, the shaping panel 130 is able to secure the position of the breast 20 toward the midline 14 of the body without allowing the shaping panel 130 to stretch to allow the breast 20 to move laterally away from the desired position. In some embodiments, the lateral support tab 138 may include a first pull tab portion 139 and a second pull tab portion 140 that extends laterally beyond the first pull tab portion 139. The first pull tab portion 139 may be positioned higher toward an armpit of the user, accordingly a shorter tab may provide more comfort and a lower likelihood of the arm interfering with the attachment of the first pull tab portion 139. The second pull tab portion 140 may attach lower down the torso of the user, where the user's arm is less likely to inadvertently contact the second pull tab portion 140. The height and width of the lateral support tab 138 may be based on both the user's cup size and band size. For example, the height of the lateral support tab 138 may be based on the user's cup size with larger cup sizes needing a greater amount of lateral support to hold the breast 20 in position for the desired amount of cleavage. The lateral width of the lateral support tab 138 may be based on the user's band size with a broader torso needing a greater width to lock the tissue into place. FIGS. 5I and 5J illustrate the lateral support tab 138 attached to a user 10.

As noted above, in some embodiments, it is contemplated that the base anchoring portion 120 may be integral with the shaping panel 130. To provide variety elasticity between the base anchoring portion 120 and the shaping panel 130 in such embodiments, the adhesive fabric may be woven so as to provide varying directions of elasticity. For example, the base anchoring portion 120 pay the woven so as to provide lateral stretching while the shaping panel 130 may be woven so as to provide vertical stretching.

It is noted than that various edges of the adhesive support garment 100 may be round to provide for a smoother application and a more comfortable fit.

Referring to FIGS. 5A-5L, a method of application and wear of the adhesive support garment 100 is generally depicted. As illustrated in FIGS. 5A and 5B, the base anchoring portion 120 is attached to the torso 11 of the user 10 beneath the breast 20. As noted herein, the removable backing layer 110 may indicate the order of application of the various parts of the adhesive support garment 100. In manufacturing, the removable backing layer 110 may be cut in an application pattern and marked to indicate the application order for applying the adhesive support garment 100. In the present embodiment, the removable backing layer 110 of the base anchoring portion 120 is labeled 1. To attach the base anchoring portion 120, the labeled backing section 1 of the removable backing layer 110 is removed to expose the adhesive layer 103. The adhesive layer 103 is then contacted to the body as described above.

After application of the base anchoring portion 120, the shaping panel 130 may be attached to the breast 20. In doing so, the shaping panel 130 may extend from the base anchoring portion 120 to hold and orient the breast 20 as desired by the user. The finished application is illustrated in FIG. 5K. However, as noted above, the shaping panel 130 may include a number of portions that may be positioned in order to support the breast 20. In particular, as shown in FIGS. 5C and 5D, the panel anchor portion 132 as indicated by labeled backing section 2 of the removable backing layer 110 may be attached to the base anchoring portion 120. To attach the panel anchor portion 132 to the base anchoring portion 120, the labeled backing section 2 of the removable backing layer 110 may be removed to expose the adhesive of the panel anchor portion 132. Accordingly, the panel anchor portion 132 may be adhered to the base anchoring portion 120 with the adhesive.

At this point, the labeled backing section 3 of the removable backing layer 110 may be removed from the lifting panel portion 134, as illustrated in FIG. 5E. The lifting panel portion 134 may then be stretched over the breast 20 to lift the breast 20 to the desired position and adhered to the breast 20. Upon positioning of the lifting panel portion 134, the labeled backing section 4 of the removable backing layer 110, may be removed from the vertical grip and support tab 136 and the vertical grip and support tab 136 may be smoothed into place to fortify the shaping panel 130, as illustrated in FIGS. 6G and 6H. As illustrated in FIGS. 5I and 5J, the labeled backing section 5 of the lateral support tab 138 may be removed and secured to the side of the user 10. Prior to securing the lateral support tab 138 into place, the user may adjust the lateral position of the breast 20 to provide the desired amount of cleavage, whereupon the lateral support tab 138 may be adhered to the user.

It is noted that application to the second breast 20 may be substantially identical to that described above. In some cases however, due to natural variations in breast tissue between the right and left breast, each breast may be separately adjusted to provide a more uniform appearance. Moreover, each breast support portion 101a, 101b may be modified in size and/or shape to accommodate/customize the fit of the adhesive support garment 100 to the particular wearer's breasts.

In some embodiments, an insert (e.g., silicone, foam, or the like) may be worn underneath the adhesive support garment to provide additional volume and/or shaping to a user's breast.

Figure 5L:
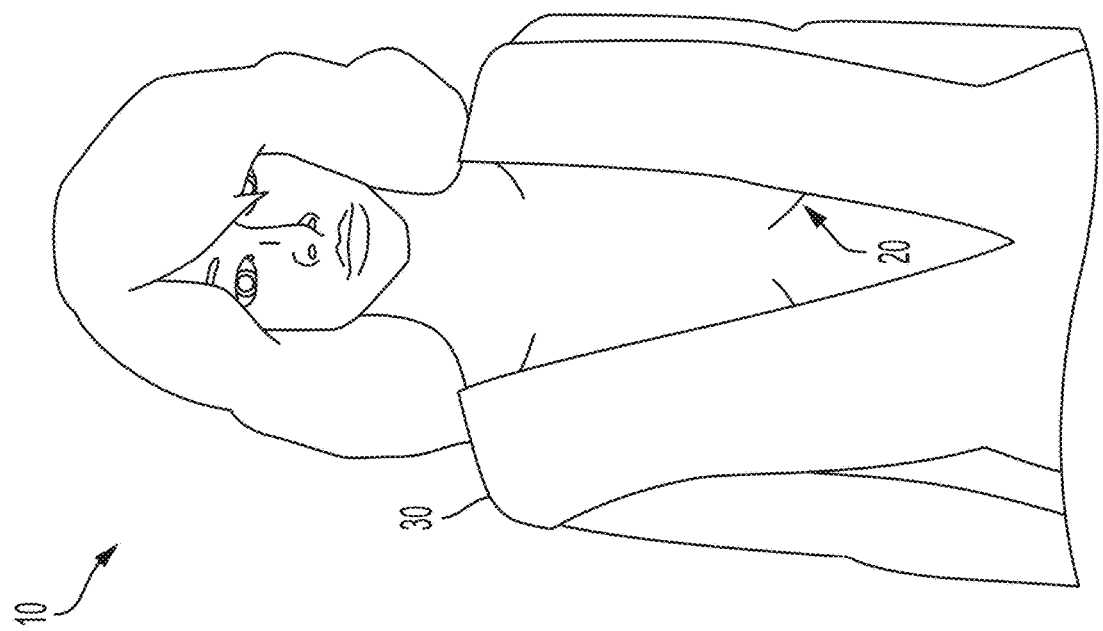
FIG. 5L depicts the user dressed with the adhesive support garment substantially undetectable beneath the clothing, according to one or more embodiments shown and described herein.
Figure 5K:
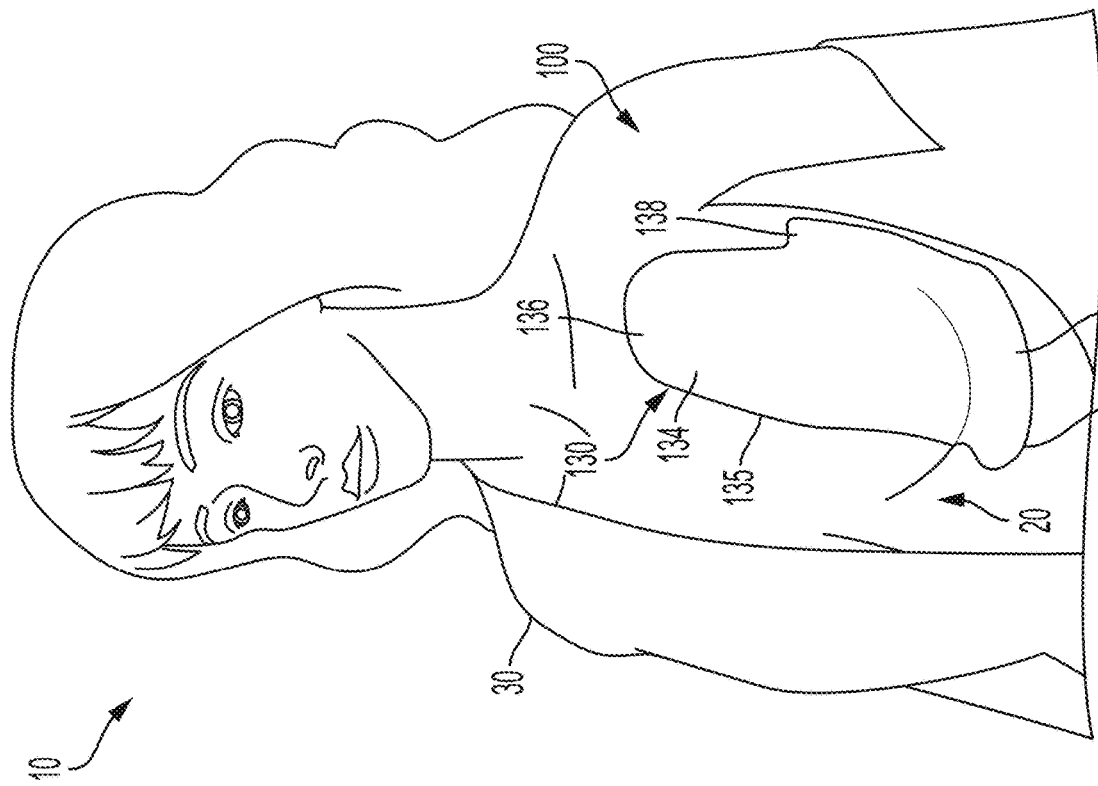
FIG. 5K depicts a perspective view of the adhesive support garment as applied to a user, according to one or more embodiments shown and described herein.

FIGS. 5K and 5L illustrate the adhesive support garment 100 under a garment 30 with a plunging neckline. As illustrated in FIG. 5L the adhesive support garment 100 is visually undetectable under the garment 30.

Manufacturing of the adhesive support garment 100 may be achieved in many ways. In a particular embodiment, a method of manufacturing the adhesive support garment 100 includes providing an adhesive material as described above and cutting out a shape of the adhesive support garment 100 from the adhesive material. The shape variations of the adhesive support garment 100 may, as described above be based on the cup and band size of the particular user, which may be provided when the user is ordering the adhesive support garment. The method may further include cutting the backing of the adhesive material in an application pattern as described above. For example, and as illustrated above, the application pattern may be marked to indicate an application order for applying the adhesive support garment 100.

Figures 6A, 6B:
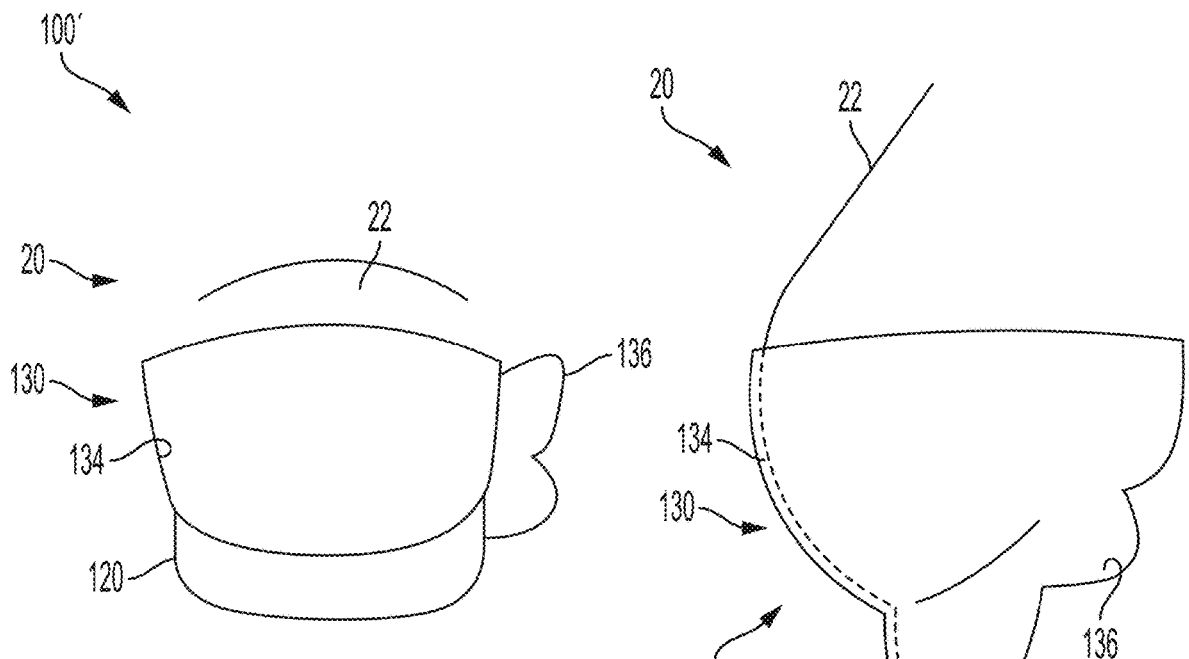
FIG. 6A depicts a strapless adhesive support garment, according to one or more embodiments shown and described herein.
FIG. 6B depicts a side view of the strapless adhesive support garment of FIG. 6A, according to one or more embodiments shown and described herein.
Figures 7A, 7B:
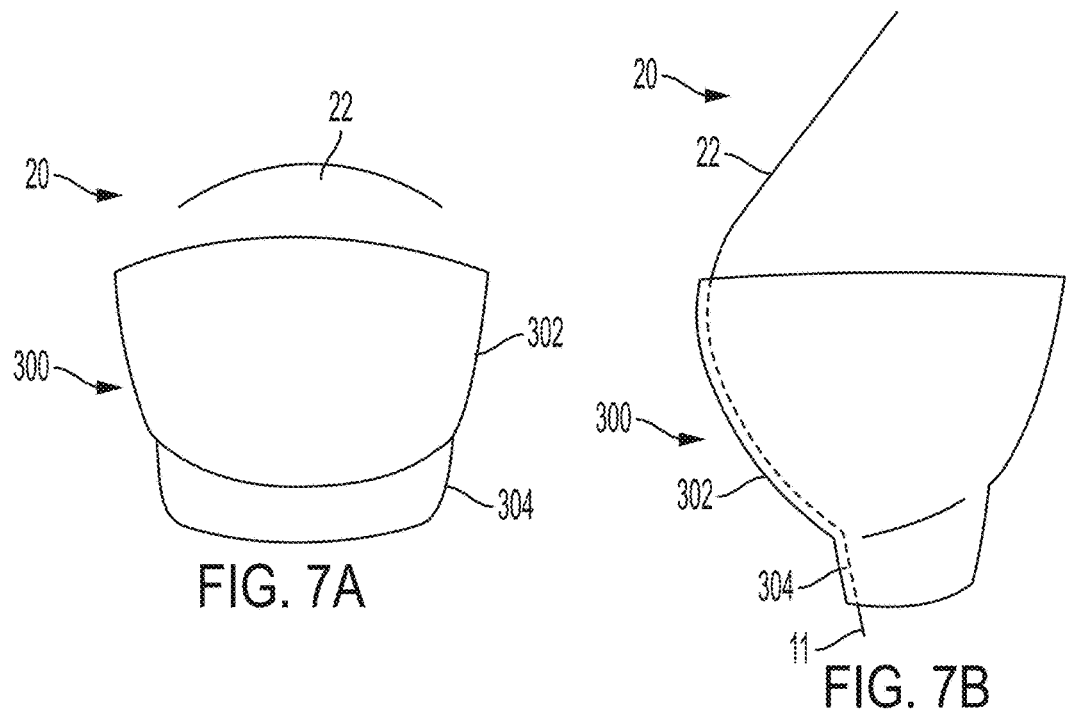
FIG. 7A depicts a pre-formed cup to be worn by a user beneath an adhesive support garment, according to one or more embodiments shown and described herein.
FIG. 7B depicts a side view of the pre-formed cup of FIG. 7A, according to one or more embodiments shown and described herein.

Various modifications of the present design are contemplated. For example, in some embodiments, a preformed cup (e.g., vacuum formed plastic, foam, etc.) may be positioned over the breast 20 to provide additional shaping and or volume to the user's breast. FIGS. 6A-6B illustrate this concept with a strapless embodiment 100' of the adhesive support garment 100. FIGS. 7A and 7B illustrate the preformed cup 300 having a cupping portion 302 which cups the breast 20. In some embodiments, attached to the cupping portion 302 may be a support portion 304 and engages the user's trunk 11 beneath the breast 20. The adhesive support garment 100 may then be layered over the preformed cup 300 and breast 20 as described above.

In other embodiments, moldable fibers 400 (e.g., plastic fibers), as illustrated in FIGS. 8A-8D, may be woven into the adhesive material and then pre-formed (e.g., vacuum formed) into a cup shape to aid in shaping the user's breast. In yet further embodiments, the adhesive material may include a top fabric layer 402 above the woven fiber layer 404 and in between the top fabric layer and the woven fabric layer may be pre-formed wires/molded fibers to provide additional shaping to the user's breast. The molded fibers 400 may provide an underwire 406 and/or a cup 408 type structure. In some embodiments, and as illustrated in FIGS. 8C and 8D, the molded fibers 400 may extend below the breast 20 and along the user's trunk 11, to provide additional support.

It should now be understood that the embodiments described herein are directed to adhesive support garments, methods of application, and methods of manufacture. In particular, the adhesive support garments described herein allows a user to wear garments that would otherwise reveal traditional support garments (e.g., bras having straps and a horizontal band) while having desired coverage, lift, and support. Such garment is also substantially seamless under clothing, so as to provide a wearer with a desired silhouette. Such adhesive support garments may be worn beneath attire having plunging necklines and/or backless ensembles while remaining unseen. Furthermore, such adhesive support garments may be easy to apply to user such that a user may easily apply the garment to oneself without the need for additional help from others.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An adhesive support garment comprising:
a base anchoring portion comprising an elongate strip having a strip width defining a strip width direction and a strip length greater than the strip width and defining a strip length direction, the base anchoring portion configured to be adhered to a body of a wearer beneath a breast of the wearer, the elongate strip configured to be elastically deformable along the strip length direction and relatively inelastic along the strip width direction; and
a shaping panel comprising a fabric layer and an adhesive layer, the shaping panel comprising a panel width defining a panel width direction and a panel height defining a panel height direction, the shaping panel being contoured in the panel height direction to be arranged substantially parallel to a midline of the wearer, the shaping panel comprising a lifting panel portion, the shaping panel being configured to overlap with and extend from the base anchoring portion over the breast and adhere to the breast such that the panel width direction is oriented substantially parallel to the strip length direction, the lifting panel portion comprising a pattern of elasticity causing the lifting panel portion to be elastically deformable in the panel height direction to lift and orient the breast in the panel height direction, wherein the shaping panel comprises:
a panel anchor portion configured to adhere to the base anchoring portion wherein the lifting panel portion extends from the panel anchor portion,
a vertical grip and support tab extending vertically above the lifting panel portion, and
a lateral support tab extending laterally from the lifting panel portion, the lateral support tab comprises: a first pull tab portion and a second pull tab portion that extends laterally beyond the first pull tab portion,
wherein the first pull tab portion and the second pull tab portion extend from the lifting panel portion in the panel width direction so as to be oriented toward an underarm of a user, wherein the second pull tab portion extends beyond the first pull tab portion in the panel width direction.

2. The adhesive support garment of claim 1, wherein the base anchoring portion comprises a tissue attachment surface and a panel attachment surface opposite the tissue attachment surface, wherein the shaping panel adheres to the panel attachment surface.

3. The adhesive support garment of claim 1, wherein the shaping panel is substantially inelastic along the panel width.

4. The adhesive support garment of claim 1, further comprising a removable backing layer.

5. The adhesive support garment of claim 4, wherein the removable backing layer includes at least one marking to indicate an order of application of the adhesive support garment.

6. A method of applying an adhesive support garment, the method comprising:
attaching a base anchoring portion of a torso of a user beneath a breast of the user, the base anchoring portion comprising an elongate strip having a strip width defining a strip width direction and a strip length greater than the strip width and defining a strip length direction, the base anchoring portion configured to be adhered to a body of a wearer beneath a breast of the wearer, the elongate strip configured to be elastically deformable along the strip length direction and relatively inelastic along the strip width direction; and
attaching a shaping panel to the breast, the shaping panel comprising a fabric layer and an adhesive layer, the shaping panel comprising a panel width defining a panel width direction and a panel height defining a panel height direction, the shaping panel being contoured in the panel height direction to be arranged substantially parallel to a midline of the wearer, the shaping panel comprising a lifting panel portion, the shaping panel being configured to overlap with and extend from the base anchoring portion over the breast and adhere to the breast such that the panel width direction is oriented substantially parallel to the strip length direction, the lifting panel portion comprising a pattern of elasticity causing the lifting panel portion to be elastically deformable in the panel height direction to lift and orient the breast in the panel height direction,
wherein the shaping panel comprises:
a panel anchor portion configured to adhere to the base anchoring portion wherein the lifting panel portion extends from the panel anchor portion;
a vertical grip and support tab extending vertically above the lifting panel portion; and
a lateral support tab extending laterally from the lifting panel portion,
wherein the base anchoring portion comprises a tissue attachment surface and a panel attachment surface opposite the tissue attachment surface, wherein the shaping panel adheres to the panel attachment surface, the shaping panel comprises a backing layer configured to extend over the adhesive layer, the backing layer comprises:
a first labeled backing section corresponding with the panel anchor portion;
a second labeled backing section corresponding with the lifting panel portion,
a third labeled backing section corresponding with the vertical grip and support tab; and
a fourth labeled backing section corresponding with the lateral support tab.

7. The method of claim 6, wherein attaching the shaping panel to the breast comprises:
adhering the panel anchor portion to the base anchoring portion, after the base anchoring portion is attached to the torso;
stretching the lifting panel portion over the breast and attaching it thereto;
securing the lifting panel portion by adhering the vertical grip and support tab to the user; and
securing the lateral support tab to a side of the user.

8. An adhesive support garment comprising:
a base anchoring portion comprising an elongate strip having a strip width defining a strip width direction and a strip length greater than the strip width and defining a strip length direction, the base anchoring portion configured to be adhered to a body of a wearer beneath a breast of the wearer, the elongate strip configured to be elastically deformable along the strip length direction and relatively inelastic along the strip width direction; and a shaping panel comprising a fabric layer and an adhesive layer, the shaping panel comprising a panel width defining a panel width direction and a panel height defining a panel height direction, the shaping panel being contoured in the panel height direction to be arranged substantially parallel to a midline of the wearer, the shaping panel comprising a lifting panel portion, the shaping panel being configured to overlap with and extend from the base anchoring portion over the breast and adhere to the breast such that the panel width direction is oriented substantially parallel to the strip length direction, the lifting panel portion comprising a pattern of elasticity causing the lifting panel portion to be elastically deformable in the panel height direction to lift and orient the breast in the panel height direction, wherein the shaping panel comprises:

a panel anchor portion configured to adhere to the base anchoring portion wherein the lifting panel portion extends from the panel anchor portion;

a vertical grip and support tab extending vertically above the lifting panel portion; and a lateral support tab extending laterally from the lifting panel portion, wherein the base anchoring portion comprises a tissue attachment surface and a panel attachment surface opposite the tissue attachment surface, wherein the shaping panel adheres to the panel attachment surface, the shaping panel comprises a backing layer configured to extend over the adhesive layer, the backing layer comprises:

a first labeled backing section corresponding with the panel anchor portion;

a second labeled backing section corresponding with the lifting panel portion, a third labeled backing section corresponding with the vertical grip and support tab; and a fourth labeled backing section corresponding with the lateral support tab.

9. The adhesive support garment of claim 8, wherein the shaping panel is substantially inelastic along the panel width.

10. The adhesive support garment of claim 8, further comprising a removable backing layer.

11. The adhesive support garment of claim 10, wherein the removable backing layer includes at least one marking to indicate an order of application of the adhesive support garment.

* * * * *